(12) United States Patent
Staali et al.

(10) Patent No.: US 11,259,953 B2
(45) Date of Patent: Mar. 1, 2022

(54) FEMALE SMART WEARABLE SYSTEM FOR URINE INCONTINENCE MANAGEMENT

(71) Applicants: Amine Staali, Mazouna (DZ); Souheil Guessoum, Algiers (DZ)

(72) Inventors: Amine Staali, Mazouna (DZ); Souheil Guessoum, Algiers (DZ)

(*) Notice: Subject to any disclaimer, the term of this patent is extended or adjusted under 35 U.S.C. 154(b) by 85 days.

(21) Appl. No.: 15/929,974

(22) Filed: Jun. 1, 2020

(65) Prior Publication Data
US 2020/0375781 A1 Dec. 3, 2020

Related U.S. Application Data

(60) Provisional application No. 62/854,334, filed on May 30, 2019.

(51) Int. Cl.
*A61F 5/441* (2006.01)
*A61M 1/00* (2006.01)
*A61M 3/02* (2006.01)
*A61F 5/455* (2006.01)

(52) U.S. Cl.
CPC .......... *A61F 5/441* (2013.01); *A61M 1/0023* (2013.01); *A61M 3/0258* (2013.01); *A61F 5/455* (2013.01); *A61M 2205/3334* (2013.01); *A61M 2205/502* (2013.01); *A61M 2209/088* (2013.01); *A61M 2210/1092* (2013.01)

(58) Field of Classification Search
CPC .......... A61F 5/441; A61F 5/455; A61M 1/71; A61M 3/0258; A61M 2209/088; A61M 2202/0496; A61M 2210/1092; A61M 2205/3334
See application file for complete search history.

(56) References Cited

U.S. PATENT DOCUMENTS

| 4,281,655 A | * | 8/1981 | Terauchi ................. A61F 5/451 4/305 |
| 4,563,183 A | | 1/1986 | Barrodale et al. |
| 6,238,378 B1 | * | 5/2001 | Perez ................... A61F 5/4404 604/317 |
| 6,592,560 B2 | | 7/2003 | Snyder |

(Continued)

FOREIGN PATENT DOCUMENTS

| EP | 0610638 A1 | * | 8/1994 | ............... A61F 5/44 |
| GB | 2490327 A | | 10/2012 | |

*Primary Examiner* — Susan S Su
*Assistant Examiner* — Eric Rassavong

(57) ABSTRACT

A female smart wearable system for management of urine incontinence comprising of a female urinary external catheter to allow urine to drain without obstruction, provided with a stabilizer for supporting and bounding/confining the external catheter in the contour of female genitalia and a urine collection device which is either having a plurality of vertical chambers for collecting urine as well as supplying fluid to keep the subject clean in a more convenient and hygienic way or is having a disposable pad for female subject with moderate or low urinary incontinence. The female smart wearable system is worn by the female subject in an underwear integrated with plurality of sensors that provide data to help in understanding and preventing the problem of urine incontinence. The female smart wearable system integrates provision of washing inside the device and use of disposable pads makes it cost effective and reusable.

14 Claims, 13 Drawing Sheets

(56) References Cited

U.S. PATENT DOCUMENTS

| | | | | |
|---|---|---|---|---|
| 8,046,848 B2* | 11/2011 | Birbara | ................. | A61G 9/006 |
| | | | | 4/144.1 |
| 9,737,433 B2* | 8/2017 | Joh | ......................... | A61F 5/453 |
| 10,799,386 B1* | 10/2020 | Harrison, Sr. | ........ | A61F 5/4408 |
| 2003/0181880 A1* | 9/2003 | Schwartz | ............. | A61G 5/1054 |
| | | | | 604/358 |
| 2015/0257925 A1 | 9/2015 | Schwartz | | |
| 2016/0095684 A1* | 4/2016 | Berryman | ......... | A61F 13/47227 |
| | | | | 600/29 |
| 2016/0113809 A1 | 4/2016 | Kim | | |
| 2017/0196726 A1* | 7/2017 | SanAntonio | .......... | A61F 5/4405 |
| 2019/0247221 A1* | 8/2019 | Doherty | ............... | A61F 5/4408 |

* cited by examiner

FEMALE SMART WEARABLE SYSTEM FOR URINE INCONTINENCE MANAGEMENT

FIELD OF THE INVENTION

The present invention relates to a non-invasive system for management of urinary incontinence in a female subject. More particularly, it relates to a urinary external catheter for draining the urine, said external catheter being provided with a stabilizer for bounding/confining the external catheter in the contour of female genitalia. The external catheter is further provided with a multi-chambered device for collecting urine as well as supplying fluid to keep the subject clean in a more convenient and hygienic way.

BACKGROUND OF THE INVENTION

Urinary incontinence is a disease condition that can affect both men and women at any age, but largely affects geriatric patients due to change in functionality of internal organs. The internal organs may behave abnormally due to many reasons like degeneration of tissues, hormonal changes, metabolism and/or any surgical intervention. Urinary incontinence is a specific condition where involuntary muscles of the urinary bladder lose strength and sphincter muscles lose control resulting in continuous leakage of urine from the bladder. It is known in the state of the art that between 15 and 35% of the old age population particularly ages over 60 years old are more prone to this condition. With advancement of the age, the prevalence of disease increases. Urinary incontinence in women is the unintentional loss of urine. It occurs often in women than in men. Pregnancy, childbirth, and menopause may contribute to urinary incontinence in women. Weak bladder muscles, overactive bladder muscles, and nerve damage may also cause urinary incontinence in women. Urinary incontinence in women is a common and treatable condition. There are different types of urinary incontinence conditions in women, including stress incontinence, urge incontinence, overactive bladder, functional incontinence, overflow incontinence, mixed incontinence, and transient incontinence.

Diagnosis of urinary incontinence in women may involve a physical exam, an ultrasound and tests including cystoscopy, urinalysis and a bladder stress test. Treatment of urinary incontinence in women may include behavioral or non-pharmacologic treatments like bladder training and Kegel exercises, medication, biofeedback, neuromodulation, surgery, catheterization or a combination of these therapies.

An external catheter is a thin, flexible tube that a person temporarily inserts into their bladder through the urethra to drain the urine from the bladder. The external end of this tube may be left open, allowing the urine to drain into an external drainage bag which collects the urine. The method of inserting the tube inside the urethra is an invasive method.

GB2490327A discloses a pumped urine collection system comprising of a pump, a power source, a urine detection sensor, and a urine collection bag. The system may be fitted to a belt around the waist. The system can be adapted to be suitable for both males and females by attaching a commercially available male sheath or specially constructed female urine collection funnel (FIGS. 3 & 4). The urine collection bag may consist of a number of inter-linked compartments 24 to prevent audible sounds of liquid movement. The main drawback of the invention is that the probability of urine infection is high as urine gets collected in the urine collection bag which gets in touch with female urethra.

US20160113809A1 discloses an automatic urine collection device which comprises a urine collecting unit for collecting urine from a user and spraying a cleansing water to a urination part, a housing comprising a urine storage unit for storing the urine collected from the urine collecting unit, a cleansing water storage unit for storing the cleansing water used in the urine collecting unit, a driving unit for moving the urine in the urine collecting unit to the urine storage unit and moving the cleansing water in the cleansing water storage unit to the urine collecting unit, a control unit for controlling an operation of the driving unit, a filtration unit, and a housing sensor unit including sensors for detecting a urine level of the urine storage unit, a cleansing water level of the cleansing water storage unit, and a temperature of the cleansing water; and an operational panel for manipulating a control and checking a state of the control unit. The said apparatus allows a patient to urinate as well as wash the urination part by himself/herself without help of a caregiver. It enables a bedridden patient to wash the urination part with the cleansing water after urination for sanitary purpose and relieves the mental and economic burdens by minimizing urinary tract infections, and prevents any offensive odor during use by equipping a deodorizing means for removing the offensive odor released through the air outlet of the urine storage unit in which the urine is stored. The main drawback of the invention is that the system is more complicated due to the use of various sensors.

CN204890301U discloses a utility model that is a female urinary device for preventing leakage, belonging to the field of clinical care products. The utility model comprises a fixing member, urine receiving body, an infusion tube and a urine storage container. The urine receiving body is worn on the patient through a fixing member, and the urine receiving body is connected to the urine storage container through the infusion tube, and the urine collecting body. The utility model is made of a flexible material, and the urinary body is provided with a venting hole, and the urinary body is provided with a rigid supporting ring which is tightly fixed with the interior of the urinary body and is rigidly supported. The ring is provided with a "V" shaped groove corresponding to the position of the venting hole of the urinary body, and the "V" shaped groove and the venting hole form an open downward venting passage. The utility model utilizes a "V" shaped groove on the rigid support ring to block the vent hole on the main body of the urinary device, thereby avoiding leakage of urine from the vent hole, and preventing the hard support ring from blocking the vent hole, thereby ensuring good gas permeability inside the body of the urine collector. The main drawback of the invention is that it does not mention any provision for cleaning and the arrangement provided does not support movement of patient.

US20150257925A1 describes the gel and non-gel structures for interfacing with various portions of an organism's body are disclosed. A gel structure such as a web-like structure is configured to encircle a portion of the human body. The gel structure can be adapted to encircle virtually any exterior or interior portion of the human body. The gel structure can interface with an external medical device for delivery of medicine or for extracting substances and fluids from the human body. The main drawback of the invention is the use of gel-based structures which is highly infectious for human body.

U.S. Pat. No. 6,592,560B2 discloses a feminine care device for collecting urine including a reservoir defining a recess for receiving the urine. The reservoir has a rim and flange configured for periurethral sealing and adhesion to the labia minora, respectively. A tab depends from the reservoir for engagement and adhesion to the anterior vaginal wall. A drain for selectively draining urine from the reservoir is provided. The main drawback of the invention is that this works in an invasive mode to stabilize and further in order to place this device, the whole area of vagina has to be contacted by hand (gloves) to clean before and after placing which involves risk of transmitting the bacteria both ways and frequent cleaning (usually done with anti-septic) weakens the immune system and creates high tolerance within inside skin.

U.S. Pat. No. 4,563,183A discloses a female external catheter which includes an intralabial flange with an adhesive body on one side and an outwardly extending urinary tube on the other side. The adhesive body is adapted to adhere to and seal with the tissue of the vestibule of a female patient around the urethral meatus and vaginal introitus and occlude the introitus. The urinary tube has a bore that extends through the flange and adhesive body to surround the urethral meatus and isolate it from the introitus. A vent is provided for venting the vagina. The main drawback of this invention is that it is an invasive foley catheter for urinary retention which is different than urinary incontinence. The invention is not suitable for the issue of urinary incontinence. Also, issues relating to adhesive exist.

Hence, in state of the art most of the urine management systems and catheter are either invasive due to which the subject finds difficulty in carrying out daily activities or they involve a risk factor of developing a bacterial infection or skin infection due to frequent involvement of hands or the adhesive used. Further, some techniques in state of the art are such that they involve complex machinery that increases the cost by multiple times.

Therefore, there is a need of non-invasive urine management system for female subject which helps in passing the urine as well as keeps the urination part clean without any obstruction and collecting the urine in a hygienic and convenient way. In addition, there is a need of a technology that is cost effective and involves least risk of infections.

OBJECT OF THE INVENTION

The main object of the present invention is to provide a system for management of urine incontinence in a female subject.

Yet another object of the present invention is to provide a comfortable and wearable female urinary external catheter that allows the urine to pass into a urine collection device without any obstruction and enables the female subject to carry on day to day tasks.

Yet another object of the present invention is to provide a multi-chambered device for collecting urine in a convenient and hygienic way.

Yet another object of the present invention is to provide a multi-chambered device for supplying water for washing the urinary area of the female body.

Still another object of the present invention is to provide a stabilizer for securing the external catheter position to comfortably fit in the contour of female genitalia.

SUMMARY OF THE INVENTION

The present invention relates to a non-invasive system for management of urinary incontinence in a female subject. More particularly, it relates to a wearable and comfortable female urinary external catheter to allow the urine to pass, a stabilizer for bounding/confining the female urinary external catheter in the contour of female genitalia and a multi-chambered device for collecting urine and supplying fluid for washing in a more convenient and hygienic way.

In a preferred embodiment, the present invention provides a system for management of urinary incontinence comprises of a female urinary external catheter to allow urine to drain without any obstruction, provided with a stabilizer for supporting and bounding/confining the external catheter in the contour of female genitalia and a urine collection device having a plurality of vertical chambers for collecting urine and storing a fluid preferably water for cleaning the urinary area of the female subject.

In another preferred embodiment, the present invention provides a system for management of urinary incontinence for a female subject with moderate or low urinary incontinence comprising of a female urinary catheter to allow a low flow of urine or urine drops to drain out, provided with a stabilizer for supporting and for supporting and bounding/confining the external catheter in the contour of female genitalia and a urine collection device which is a highly absorbent pad enclosed in a water resistant cover with an extension line/string that comes in contact with the urine inside the isolation chamber and absorbs and eventually moved to the pad. A collection device with plurality of vertical chambers for storing fluid preferably water for cleaning the urinary area of the female subject is optionally worn on waist.

In yet another embodiment, the present invention provides a female urinary external catheter wearable with underwear comprising of an upper portion and a lower portion. The upper portion comprises of a holding apparatus, an isolation chamber, a spraying apparatus, a plurality of inlets and an air vent. The lower portion comprises of an outlet, an air discharge tube and a plurality of strap for fixing the female urinary external catheter to the underwear. The holding apparatus is having an inflatable wall bordered around urethral orifice of the female subject and a soft jelly wall surrounded around the inflatable wall forming an outer surface of the female urinary external catheter. The isolation chamber is a hollow urinal basin between the inflated wall and the jelly wall through which the urine passes towards the urine collection device. The plurality of inlets is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall. The inlet for air is positioned adjacent to the inlet of water on the outer surface of the jelly wall and connected to an air pump tube of the pump for pumping the air to the inflatable wall. Further, an air vent adjacent to the inlet of air is provided to push the air from the external catheter. The air discharge tube in the lower portion is connected to the inflatable wall forming a continuous channel for discharging the air from the inflatable wall. The outlet in the lower portion is provided on the outer surface of the female urinary external catheter to drain the urine to a urine collection device or urine bag attached externally. Further, the plurality of strap preferably Velcro strap extend from the two ends of the outer surface of the female urinary external catheter to fix it with the underwear. The underwear is integrated with a plurality of sensors for collecting information about muscle movements and understanding the position of female subject while the urine loss happens. The collected information gives accurate synergies to understand the root of the problem and craft a life style to prevent the problem. In yet another alternative embodiment, the present invention provides a female urinary external catheter wearable with underwear comprising of an upper portion and a lower portion. The upper portion comprises of a holding apparatus, an isolation chamber, a spraying apparatus, a plurality of inlets and a patch sensor. The lower portion comprises of an outlet and a plurality of strap for fixing the female urinary external catheter to the underwear. The holding apparatus is having a soft jelly wall forming an outer surface of the external catheter. The isolation chamber is a hollow urinal basin inside the jelly wall through which the urine passes towards the urine collection device. The patch sensor is a disposable adhesive patch inside the isolation chamber which senses the fluid in the isolation chamber. The plurality of inlet is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall. The outlet for urine is positioned on the outer surface of the jelly wall adjacent to the inlet of water and connected to the pump for pumping the urine to a urine collection device. The outlet acts as a urine sucking hole and when the urine enters the isolation chamber, it is sensed by the sensor patch and gets pumped into the urine collection device through the pump. The urine collection device is in the form of a belt worn around the waist of a female subject and locked with the help of a belt lock. A data transmitter chip is integrated and powered in the belt connected with patch sensor located in the female urinary external catheter and synchronized with a urine flowmeter located in the tube for sucking the urine/water. The data transmitter chip, patch sensor and urine flow meter are into a continuous data collection and transmission to an information collection system such as a mobile with an inbuilt application that reads and displays characteristics of urine flow such as flow, timing, quantity and sequence of urine loss. This inbuilt application acts as a personal urologist assistant and helps in understanding the issue and identifying the patterns that helpful in treatment of the female subject. The underwear is integrated with a plurality of sensors for collecting information about muscle movements and understanding the position of female subject while the urine loss happens. The collected information gives accurate synergies to understand the root of the problem and craft a life style to prevent the problem.

In yet another alternative embodiment, the present invention provides a female urinary external catheter wearable for a female subject with moderate or low urinary incontinence with underwear comprising of an upper portion and a lower portion. The upper portion comprises of a holding apparatus, an isolation chamber, a spraying apparatus and a plurality of inlets. The lower portion comprises of an outlet and a plurality of strap for fixing the female urinary external catheter to the underwear. The holding apparatus is having a soft jelly wall forming an outer surface of the external catheter. The isolation chamber is a hollow urinal basin inside the jelly wall comprising an extension line/string through which the urine passes towards the urine collection device. The urine collection device is a highly absorbent disposable pad enclosed in a water resistant cover with an extension line/string that comes in contact with the urine inside the isolation chamber and absorbs and eventually moved to the absorbent pad. At the outer surface of the female urinary external catheter an upper and a lower pad holder is attached in which the pad is conveniently attached and after a duration of 5-6 hours is replaced to maintain the hygiene of the female subject. The upper and lower pad holder are attachment means comprising but not limited to elastic bands, button and eyelet arrangement, a plurality of snap fasteners etc. A collection device with plurality of vertical chambers for storing fluid preferably water for cleaning the urinary area of the female subject is optionally worn on waist. The plurality of inlet is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall. The outlet to insert the extension line/string of the highly absorbent pad is positioned at the bottom of the female urinary external catheter. The female urinary external catheter has a collapsible opening made of jelly outer wall surrounding a shape resistant wall preferably made of mildly hard PVC which is curved at the bottom and folded in a zig zag pattern at the top connected to a push/pull pin which when pulled opens up the collapsible opening and fits in the outer labia around the urethral orifice. When the push/pull pin is pushed the collapsible opening closes up. With help of this collapsible opening, the female subject is able to wear the female urinary external catheter in a closed position and then open the collapsible opening for a comfortable fit. The jelly wall is preferably made of silicone surrounding the collapsible opening. The underwear is integrated with a plurality of sensors for collecting information about muscle movements and understanding the position of female subject while the urine loss happens. The collected information gives accurate synergies to understand the root of the problem and craft a life style to prevent the problem.

In yet another embodiment, the present invention provides a stabilizer comprising a first forked end, a second oval end and an arm connecting said first and second end. The oval end further comprises a concave surface holding a female urinary external catheter and facing toward body of the subject, and a convex surface facing away from the body of the subject. The stabilizer is kept in place by holding the forked end at belly of the subject using a belly sticker, thus holding the female urinary external catheter in the contour of female genitalia and limiting the urine throw area for reducing the potential of infection of urine in female genitalia. The stabilizer being flexible has a right angle that helps the female external catheter to be well detachably fixed and stuck to the genitals by the bending resistance.

In yet another embodiment of the present invention, the convex surface has a plurality of holes. The inlet for water of said jelly wall of the external catheter fits into the corresponding hole in convex surface of said oval end of said stabilizer for allowing water to pass through the female urinary external catheter. The air pumping tube and air vent of the female urinary external catheter fits into the corresponding hole in convex surface of said oval end of said stabilizer. The plurality of holes in convex surface of said oval end for inlet of water and air pumping tube are positioned on upper portion of said oval end. The plurality of holes in convex surface of said oval end for attaching the plurality of strap to the external catheter and hole in convex surface of said oval end for discharge of water/urine is positioned on lower portion of said oval end. One of the holes in convex surface is acting as an outlet for discharging the water/urine from the female urinary external catheter to the urine collection device.

The forked end of the stabilizer has different fork level connections for adjusting the height of stabilizer with respect to the female subject. The fork level connections are having different level locks which get snap locked into plurality of slots in the belly sticker and said belly sticker is fixed on the female subject by a breathable adhesive.

In yet another alternative embodiment, the convex surface has a plurality of holes. The inlet for water of said jelly wall of the external catheter fits into the corresponding hole in convex surface of said oval end of said stabilizer for allowing water to pass through the female urinary external catheter. The hole in convex surface of said oval end for inlet of water is positioned on the upper portion of said oval end of stabilizer. One of the holes in convex surface of said oval end is acting as an outlet for discharging the water/urine from the female urinary external catheter. The urine/water flows from the hole in convex surface of said oval end in lower portion to the hole in upper portion of the convex surface of said oval end via a tube and gets pumped with the help of a pump into the urine collection device. The plurality of hole in convex surface of said oval end for attaching the strap to the external catheter is positioned on the lower portion of the convex surface of said oval end.

The forked end of the stabilizer has different fork level connections for adjusting the height of stabilizer with respect to the female subject. The fork level connections are having different level locks which get snap locked into plurality of slots in the belly sticker and said belly sticker is fixed on the female subject by a breathable adhesive.

In yet another alternative embodiment, the present invention provides a back stabilizer comprising a first flat end, a second oval end and an arm connecting said first and second end. The oval end further comprises a concave surface holding a female urinary external catheter facing towards the body of the subject and a convex surface facing away from the body of the subject. The stabilizer to be placed on the back side of the female subject has an arm with an acute angle ranging from 70-90 degrees of bending that helps the female external catheter to be well detachably fixed to the genitals by the bending resistance.

Said flat end of the stabilizer has a sticker which gets fixed on the back side of the female subject by a breathable adhesive. In still another embodiment, the present invention provides a urine collection device comprising of a plurality of vertical chambers for separately collecting urine and storing water and an auto pump attached to the device. Said urine collection device is in the form of a belt worn around the waist of a female subject and locked with the help of a belt lock. The plurality of chambers is having an inlet for filling water, an inlet for filling urine and an outlet for draining the urine/water. The auto pump is operated by a plurality of on/off button for energizing the pump, for sucking the urine from said isolation chamber and pushing it faster for draining and also for pushing the water to female urinary external catheter. The auto pump has a urine tube for sucking the urine and throwing it into said urine collection device through the outlet in the belt, a water tube for providing water to clean the urinary are pumped via a water supplier tube attached in the chamber of belt storing water and an air pumping tube for pumping air to inflate said inflatable wall of female urinary external catheter. Optionally, a data transmitter chip is integrated and powered in the belt connected which is in connection with a patch sensor located in the female urinary external catheter and synchronized with a urine flow meter located in the tube for sucking the urine/water. The data transmitter chip, patch sensor and urine flow meter are into a continuous data collection and transmission to an information collection system such as a mobile with an inbuilt application that reads and displays characteristics of urine flow such as flow, timing, quantity and sequence of urine loss. This inbuilt application acts as a personal urologist assistant and helps in understanding the issue and identifying the patterns that helpful in treatment of the female subject.

DETAILED DESCRIPTION OF THE INVENTION

Figure 1:
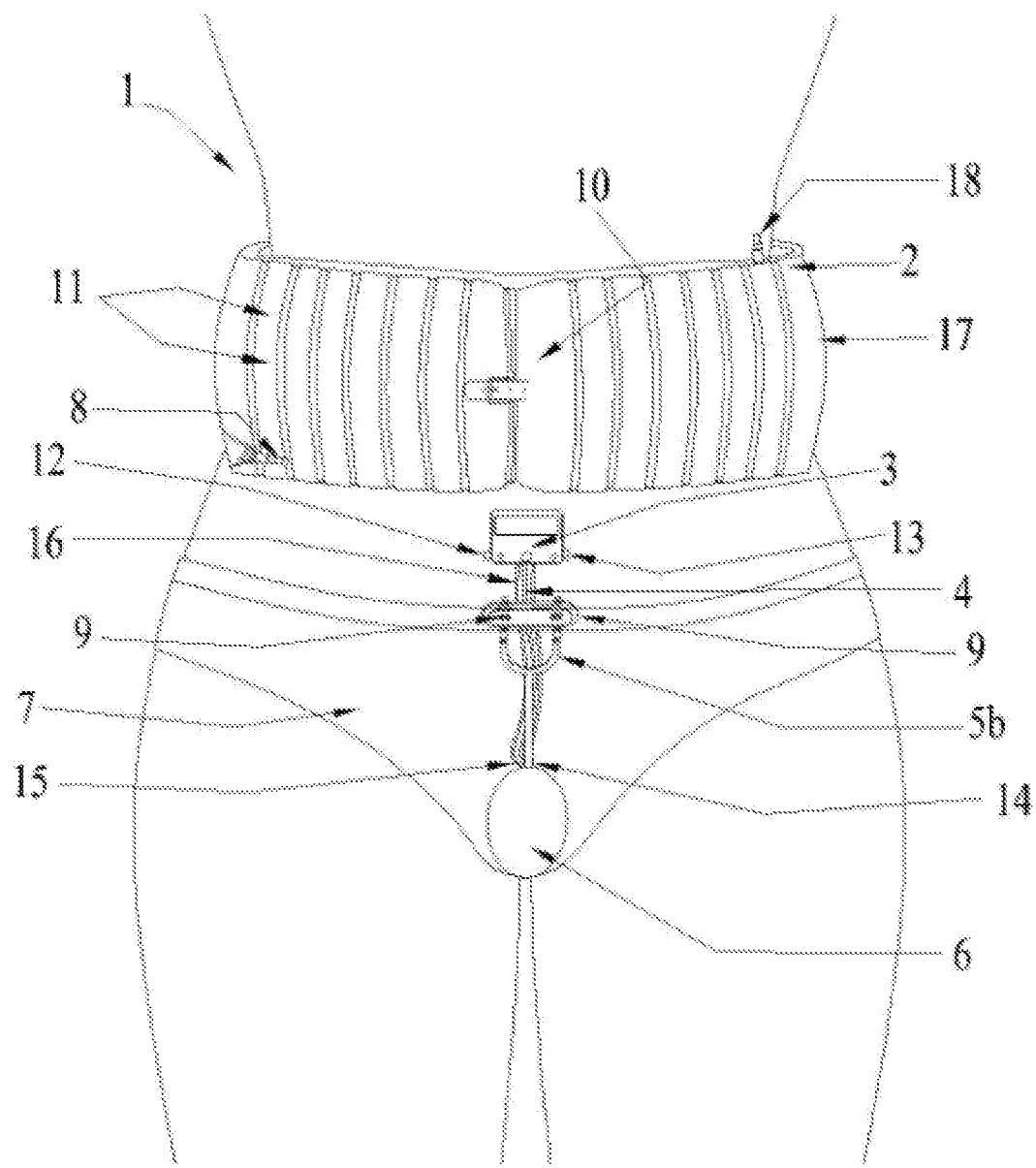
FIG. 1 is a front view of the urine management system in accordance to the embodiment of the present invention.

Many aspects of the invention can be better understood with references made to the drawings below. The components in the drawings are not necessarily drawn to scale. Instead, emphasis is placed upon clearly illustrating the components of the present invention. Moreover, like reference numerals designate corresponding parts through the several views in the drawings. Before explaining at least one embodiment of the invention, it is to be understood that the embodiments of the invention are not limited in their application to the details of construction and to the arrangement of the components set forth in the following description or illustrated in the drawings. The embodiments of the invention are capable of being practiced and carried out in various ways. In addition, the phraseology and terminology employed herein are for the purpose of description and should not be regarded as limiting.

The present invention relates to a non-invasive system for management of urinary incontinence in a female subject. More particularly, it relates to a wearable and comfortable urinary external catheter to allow the urine to pass, a stabilizer for bounding/confining the external catheter in the urinary area and a device for collecting urine and supplying fluid in a more convenient and hygienic way.

In a preferred embodiment, the present invention provides a system for management of urinary incontinence comprises of a female urinary external catheter to allow urine to drain without any obstruction, provided with a stabilizer for supporting and bounding/confining the external catheter in the contour of female genitalia and a urine collection device having a plurality of vertical chambers for collecting urine and storing a fluid preferably water for cleaning the urinary area of the female subject.

In another preferred embodiment, the present invention provides a system for management of urinary incontinence for a female subject with moderate or low urinary incontinence comprising of a female urinary catheter to allow a low flow of urine or urine drops to drain out, provided with a stabilizer for supporting and for supporting and bounding/confining the external catheter in the contour of female genitalia and a urine collection device which is a highly absorbent pad enclosed in a water resistant cover with an extension line/string that comes in contact with the urine inside the isolation chamber and absorbs and eventually moved to the pad. A collection device with plurality of vertical chambers for storing fluid preferably water for cleaning the urinary area of the female subject is optionally worn on waist.

In another preferred embodiment, the present invention provides a female urinary external catheter wearable with underwear comprising of an upper portion and a lower portion. The upper portion comprises of a holding apparatus, an isolation chamber, a spraying apparatus, a plurality of inlets and an air vent. The lower portion comprises of an outlet, an air discharge tube and a plurality of strap for fixing the female urinary external catheter to the underwear. The holding apparatus is having an inflatable wall bordered around urethral orifice of the female subject and a soft jelly wall surrounded around the inflatable wall forming an outer surface of the female urinary external catheter. The isolation chamber is a hollow urinal basin between the inflated wall and the jelly wall through which the urine passes towards the urine collection device. The plurality of inlets is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall. The inlet for air is positioned adjacent to the inlet of water on the outer surface of the jelly wall and connected to an air pump tube of the pump for pumping the air to the inflatable wall. Further, an air vent adjacent to the inlet of air is provided to push the air from the external catheter. The air discharge tube in the lower portion is connected to the inflatable wall forming a continuous channel for discharging the air from the inflatable wall. The outlet in the lower portion is provided on the outer surface of the female urinary external catheter to drain the urine to a urine collection device or urine bag attached externally. Further, the plurality of strap preferably Velcro strap extend from the two ends of the outer surface of the female urinary external catheter to fix it with the underwear. The underwear is integrated with a plurality of sensors for collecting information about muscle movements and understanding the position of female subject while the urine loss happens. The collected information gives accurate synergies to understand the root of the problem and craft a life style to prevent the problem.

The holding apparatus has an inflatable wall preferably made of silicon which fits on the contours of the urethral orifice upon inflation by pushing the air inside the inflatable wall through an auto pump. The inflatable wall gets fixed on the contour of the urethral orifice ensuring a firm hold even while doing any physical activity. The wall is inflated manually using an auto pump depending on the comfort of user. The soft jelly silicon wall surrounding the inflatable wall gives a cushioning effect to the urinary area of the female subject. The plurality of strap extending from both the ends of outer surface of the female urinary external catheter entangles on preferably a Velcro strap stitched in the underwear and is devoid of any adhesive to harm parts of female subject.

In yet another alternative embodiment, the present invention provides a female urinary external catheter wearable with underwear comprising of an upper portion and a lower portion. The upper portion comprises of a holding apparatus, an isolation chamber, a spraying apparatus, a plurality of inlets and a patch sensor. The lower portion comprises of an outlet and a plurality of strap for fixing the female urinary external catheter to the underwear. The holding apparatus is having a soft jelly wall forming an outer surface of the external catheter. The isolation chamber is a hollow urinal basin inside the jelly wall through which the urine passes towards the urine collection device. The patch sensor is a disposable adhesive patch inside the isolation chamber which senses the fluid in the isolation chamber. The plurality of inlets is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall. The outlet for urine is positioned on the outer surface of the jelly wall adjacent to the inlet of water and connected to the pump for pumping the urine to a urine collection device. The outlet act as a urine sucking hole and when the urine enters the isolation chamber, it is sensed by the sensor patch and gets pumped into the urine collection device through the pump. The urine collection device is in the form of a belt worn around the waist of a female subject and locked with the help of a belt lock. A data transmitter chip is integrated and powered in the belt connected with patch sensor located in the female urinary external catheter and synchronized with a urine flowmeter located in the tube for sucking the urine/water. The data transmitter chip, patch sensor and urine flow meter are into a continuous data collection and transmission to an information collection system such as a mobile with an inbuilt application that reads and displays characteristics of urine flow such as flow, timing, quantity and sequence of urine loss. This inbuilt application acts as a personal urologist assistant and helps in understanding the issue and identifying the patterns that helpful in treatment of the female subject. The underwear is integrated with a plurality of sensors for collecting information about muscle movements and understanding the position of female subject while the urine loss happens. The collected information gives accurate synergies to understand the root of the problem and craft a life style to prevent the problem.

In yet another alternative embodiment, the present invention provides a female urinary external catheter wearable for a female subject with moderate or low urinary incontinence with underwear comprising of an upper portion and a lower portion. The upper portion comprises of a holding apparatus, an isolation chamber, a spraying apparatus and a plurality of inlets. The lower portion comprises of an outlet and a plurality of strap for fixing the female urinary external catheter to the underwear. The holding apparatus is having a soft jelly wall forming an outer surface of the external catheter. The isolation chamber is a hollow urinal basin inside the jelly wall comprising an extension line/string through which the urine passes towards the urine collection device. The urine collection device is a highly absorbent disposable pad enclosed in a water resistant cover with an extension line/string that comes in contact with the urine inside the isolation chamber and absorbs and eventually moved to the absorbent pad. At the outer surface of the female urinary external catheter an upper and a lower pad holder is attached in which the pad is conveniently attached and after a duration of 5-6 hours is replaced to maintain the hygiene of the female subject. The upper and lower pad holder are attachment means comprising but not limited to elastic bands, button and eyelet arrangement, a plurality of snap fasteners etc. A collection device with plurality of vertical chambers for storing fluid preferably water for cleaning the urinary area of the female subject is optionally worn on waist. The plurality of inlet is positioned on the outer surface of said jelly wall. The inlet for water is connected to a water tube connect of a pump for pumping water and said inlet for water forms a continuous channel extending to the spraying apparatus to direct the water to pass through nozzles of spraying apparatus to wash the urinary area of the female subject. The spraying apparatus is positioned on the inner surface of said jelly wall and used at the time of replacing the disposable pad. The outlet to insert the extension line/string of the highly absorbent pad is positioned at the bottom of the female urinary external catheter. The female urinary external catheter has a collapsible wall and a jelly outer wall surrounding it. The collapsible wall is a shape resistant wall preferably made of mildly hard PVC which is curved at the bottom and folded in a zig zag pattern at the top connected to a push/pull pin which when pulled opens up the collapsible wall and fits in the outer labia around the urethral orifice. When the push/pull pin is pushed the collapsible wall closes up. The jelly outer wall having the collapsible wall provides a hardness to the structure that enables opening and closing by a push or pull using the resistance of the hard material of the collapsible wall. The push/pull pin for opening and closing makes the catheter contactless i.e. no direct contact is required between the female genitalia and hand (glove) of female subject. With help of this collapsible wall, the female subject is able to wear the female urinary external catheter in a closed position and then open the collapsible wall for a comfortable fit. For positioning of the catheter, it is kept in closed position and while in closed position, the jelly outer wall is placed inside the outer labia. Once the jelly outer wall of the catheter is positioned inside the outer labia and the catheter is tied with the underwear, the push/pull pin is pulled such that the collapsible wall opens along with the jelly outer wall and pushes the outer labia that eventually pulls the jelly outer wall and collapsible wall a little inside the inner labia without being invasive. Once the whole catheter is fitted and the underwear is tied up, the jelly outer wall and collapsible wall takes the shape of the inside curves of the genitalia and allow a closed area around the urethra and limits the urine flow towards the jelly outer wall after being opened. The jelly wall is preferably made of silicone surrounding the collapsible wall. The underwear is integrated with a plurality of sensors for collecting information about muscle movements and understanding the position of female subject while the urine loss happens. The collected information gives accurate synergies to understand the root of the problem and craft a life style to prevent the problem.

In yet another embodiment, the present invention provides a stabilizer comprising a first forked end, a second oval end and an arm connecting said first and second end. The oval end further comprises a concave surface holding a female urinary external catheter and facing toward body of the subject, and a convex surface facing away from the body of the subject. The stabilizer is kept in place by holding the forked end at belly of the subject using a belly sticker, thus holding the female urinary external catheter in the contour of female genitalia and limiting the urine throw area for reducing the potential of infection of urine in female genitalia. The stabilizer being flexible has a right angle that helps the female external catheter to be well positioned and stuck to the genitals by the bending resistance.

In an embodiment of the present invention, the convex surface has a plurality of holes. The inlet for water of said jelly wall of the external catheter fits into the corresponding hole in convex surface of said oval end of said stabilizer for allowing water to pass through the female urinary external catheter. The air pumping tube and air vent of the female urinary external catheter fits into the corresponding hole in convex surface of said oval end of said stabilizer. The plurality of holes in convex surface of said oval end for inlet of water and air pumping tube are positioned on upper portion of said oval end. The plurality of holes in convex surface of said oval end for attaching the plurality of strap to the external catheter and hole in convex surface of said oval end for discharge of water/urine is positioned on lower portion of said oval end. One of the holes in convex surface is acting as an outlet for discharging the water/urine from the female urinary external catheter to the urine collection device.

The forked end of the stabilizer has different fork level connections for adjusting the height of stabilizer with respect to the female subject. The fork level connections are having different level locks which get snap locked into plurality of slots in the belly sticker and said belly sticker is fixed on the female subject by a breathable adhesive.

The stabilizer having an oval end secures the outer surface of the jelly wall of the external catheter and acts like a funnel for urine to flow. The urine flows from an isolation chamber of female urinary external catheter followed by a funnel which is forming between the jelly wall of the external catheter and the oval end hence making a funneling effect. The funneling effect reduces the potential of infection of urine in female genitalia.

In yet another alternative embodiment, the convex surface has a plurality of holes. The inlet for water of said jelly wall of the external catheter fits into the corresponding hole in convex surface of said oval end of said stabilizer for allowing water to pass through the female urinary external catheter. The hole in convex surface of said oval end for inlet of water is positioned on the upper portion of said convex surface. One of the holes in convex surface of said oval end is acting as an outlet for discharging the water/urine from the female urinary external catheter. The urine/water flows from the hole in convex surface of said oval end in lower portion to the spoon hole in upper portion of the convex surface of said oval end via a tube and gets pumped with the help of a pump into the urine collection device. The plurality of hole in convex surface of said oval end for attaching the strap to the external catheter is positioned on the lower portion of the convex surface of said oval end.

The forked end of the stabilizer has different fork level connections for adjusting the height of stabilizer with respect to the female subject. The fork level connections are having different level locks which get snap locked into plurality of slots in the belly sticker and said belly sticker is fixed on the female subject by a breathable adhesive.

In yet another alternative embodiment, the present invention provides a back stabilizer comprising a first flat end, a second oval end and an arm connecting said first and second end. The oval end further comprises a concave surface holding a female urinary external catheter facing towards the body of the subject and a convex surface facing away from the body of the subject. The stabilizer to be placed on the back side of the female subject has an arm with an acute angle ranging from 70-90 degree of bending that helps the female external catheter to be well stuck to the genitals by the bending resistance. Said flat end of the stabilizer has a sticker which gets fixed on the back side of the female subject by a breathable adhesive.

In still another embodiment, the present invention provides a urine collection device comprising of a plurality of vertical chambers for separately collecting urine and storing water and an auto pump attached to the device. Said urine collection device is in the form of a belt worn around the waist of a female subject and locked with the help of a belt lock. The plurality of chambers is having an inlet for filling water, an inlet for filling urine and an outlet for draining the urine/water. The auto pump is operated by a plurality of on/off button for energizing the pump, for sucking the urine from said isolation chamber and pushing the urine out for draining and also for pushing the water to female urinary external catheter. The auto pump has a urine tube for sucking the urine and throwing it into said urine collection device through the outlet in the belt, a water tube for providing water to clean the urinary area pumped via a water supplier tube attached in the chamber of belt storing water and an air pumping tube for pumping air to inflate said inflatable wall of female urinary external catheter. Optionally, a data transmitter chip is integrated and powered in the belt connected which is in connection with a patch sensor located in the female urinary external catheter and synchronized with a urine flowmeter located in the tube for sucking the urine/water. The data transmitter chip, patch sensor and urine flow meter are into a continuous data collection and transmission to an information collection system such as a mobile with an inbuilt application that reads and displays characteristics of urine flow such as flow, timing, quantity and sequence of urine loss. This inbuilt application acts as a personal urologist assistant and helps in understanding the issue and identifying the patterns that helpful in treatment of the female subject.

The belt is preferably made of biomedical silicon material which is hypoallergenic, flexible and durable in nature.

Therefore, the urinary management system of the present invention provides three working modes wherein in first mode the urine flows from the urethral orifice and enters into an isolation chambers of the female urinary external catheter followed by a funnel formed between the spoon and the jelly wall and subsequent draining into an externally connected urine collection device and in second mode the urine flows from the urethral orifice and enters into the isolation chamber of the female urinary external catheter and is sucked from the urine outlet of the female urinary external catheter through the auto pump to the urine collection device and in third mode the urine has a low flow or just droplets which are absorbed by the urine collection device which is highly absorbent disposable pad through an extension line. In first and second mode, the urine collection device is preferably a belt having a plurality of vertical chambers to store the urine worn around the waist. The auto pump attached to the belt pushes the water through the spraying apparatus to spray the water to the urinary area of the female subject. The spraying apparatus is having a plurality of nozzles to aid in spraying/ showering the water to the urinary area. Hence, the female external catheter system is integrated with a washing system by means of a spraying apparatus which may be connected to an external bidet which is either automatically or manually operated. The catheter may work with the external bidet using a bag with an auto sucking devise as well as works with a lower urine bag worn on thigh or the leg, manually without any system that requires power for sucking. Further, in the third mode, the catheter with the disposable pad makes the system reusable and disposable combination. The use of disposable pads makes the system cost effective and contactless with the skin of the female subject thereby ensuring least risk of infection.

Now referring to FIG. 1, a front view of a female external catheter system 1 is provided. The female external catheter system 1 for managing urinary incontinence in a female subject comprises of a female urinary external catheter 6a, a stabilizer 5 and a urine collection device 17 in the form of waist belt. The female urinary external catheter 6a along with the stabilizer 5 fits inside a customized underwear 7. The female urinary external catheter 6a has an inlet 14 for water used for directing the water from the pump 3 to the female urinary external catheter 6a for spraying water to the urinary area of the female subject and has an outlet 15 for urine to pump the urine out from the female urinary external catheter 6a to the urine collection device 17 from where it is drained out. The female urinary external catheter 6a is supported by a stabilizer 5. The main function of stabilizer 5 is to bound/confine the female urinary external catheter 6a in the contour of female genitalia and limit the urine throw area consequently reducing the potential of urine infection. The stabilizer 5 has a unique fork and an oval shaped arrangement. The forked end 5b has different fork level connections for adjusting the height of stabilizer with respect to the body. The fork level connections have different level locks 9 which get snap locked into the slots of a belly sticker 101 and said belly sticker 101 is fixed on the female subject by a breathable adhesive. The urine collection device 17 is a multi-chambered device having plurality of vertical chambers 2, 11 serving the purpose of storing urine as well as water separately. It is in the form of a wearable belt and gets locked around the waist with the help of a belt lock 10. The urine collection device 17 has an inlet 18 for filling water to the water reservoir chamber of said device and an outlet 8 for draining the urine out from said device. The auto driven pump 3 attached to the belt 17 has a water pushing tube 4 for pushing the water from the device 17 to the female urinary external catheter 6a through it for washing the urinary area of female subject and a urine sucking tube 16 for sucking the urine from the female urinary external catheter 6a to the urine collection device 17 through it. The water pushing tube 4 of the auto pump 3 is connected to the inlet 14 of the female urinary external catheter 6a and the urine sucking tube 16 of the auto pump 3 is connected to the urine inlet 15 of the female urinary external catheter 6a. The urine from the urine sucking tube 16 of the auto pump 3 gets pumped and drains from the urine outlet 12 of the auto pump 3 attached to the urine collection device 17. The water pushing tube 4 of the auto pump 3 takes the water from the urine collection device 17 through the water supplier tube 13 of the auto pump 3.

Figure 2A:
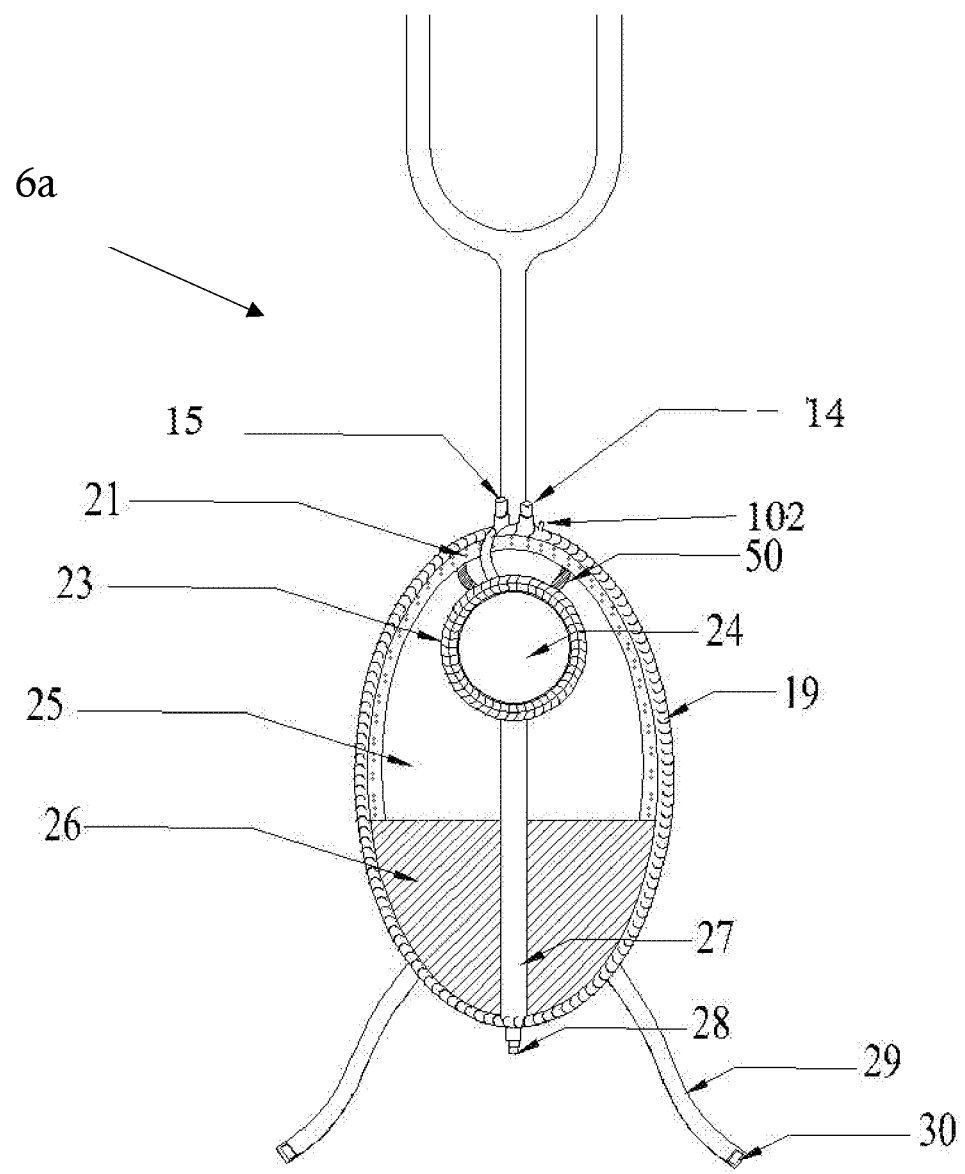
FIGS. 2a and 2b is a back view of an external catheter and an auto sucking urine external catheter in accordance to the embodiment of the present invention.

Now referring to FIG. 2a, a back view of an external catheter is provided. The external female urinary external catheter 6a has an inflatable wall 23 bordered around the urethral orifice 24 and a soft jelly wall 19 preferably made of silicone surrounding the inflatable wall 23 forming an outer surface of the external female urinary external catheter 6a. The female urinary external catheter 6a has an inlet 14 for water for directing the water from the pump to the external catheter for spraying water to the urinary area of the female body through spraying apparatus 21, an outlet 15 for urine to bump the urine out from the female urinary external catheter 6a to the urine collection device 17 and an air vent 102 to push the air from the female urinary external catheter 6a. The urine when flows from the urethral orifice 24 enters the isolation chamber 25 which is a urinal basin for temporary storing the urine and urine gets drained from the isolation chamber 25 to the urine outlet 28. The inflatable wall 23 is supported by a jelly wall 19 with the help of a focused urinal connect 50. The jelly wall 19 is made of silicone and aids the cushioning effect to the urinary area of the female subject. The lower portion of the female urinary external catheter 6a is a covered area 26 from which the air discharge tube 27 is taken out to discharge the air from an inflatable wall 23. The strap 29 is attached to the outer lower portion of the female urinary external catheter 6a with a strap connection 30 for strapping the external catheter 6a to the customized underwear 7. The strap 29 used is preferably a Velcro strap.

Hence, the female external catheter system 1 comprising: a urinary external catheter 6a to allow urine to pass down without any obstruction; a stabilizer 5 to support and hold the urinary external catheter 6a as per contour of female genitalia; and a urine collection device 17 to collect urine and store fluid for cleaning urinary area of a female subject; characterized in that, said urinary external catheter 6a is wearable and comprises of a holding apparatus, an isolation chamber 25, a spraying apparatus 21, a plurality of inlets 14, an air vent 102, an outlet 15, an air discharge tube 27 and a plurality of strap 29; said stabilizer 5 comprises of a forked end 5b, an oval end 6 and an arm 5a connecting the forked and the oval end, said oval end 6 having a convex surface facing away from the body and a concave surface facing towards body of female, and a belly sticker 101; said urine collection device 17 is a multi-chambered device attached to an auto-driven pump 3 attached to it to push the water from the urine collection device 17 for washing and to suck the urine out from the urinary external catheter 6a, the holding apparatus has an inflatable wall 23 and jelly wall 19 bordered around a urethral orifice 24, an isolation chamber 25 allows the urine to pass towards the urine collection device 17, an air vent 102 to push the air from the external catheter 6a, a spraying apparatus 21 to direct the water to wash the urinary area of female subject. The convex surface has plurality of holes 34, 35 to fit into the plurality of holes of urinary external catheter 6a. The urine collection device 17 is an external urine bag or in the form of belt worn around the waist of female subject.

Figure 2B:
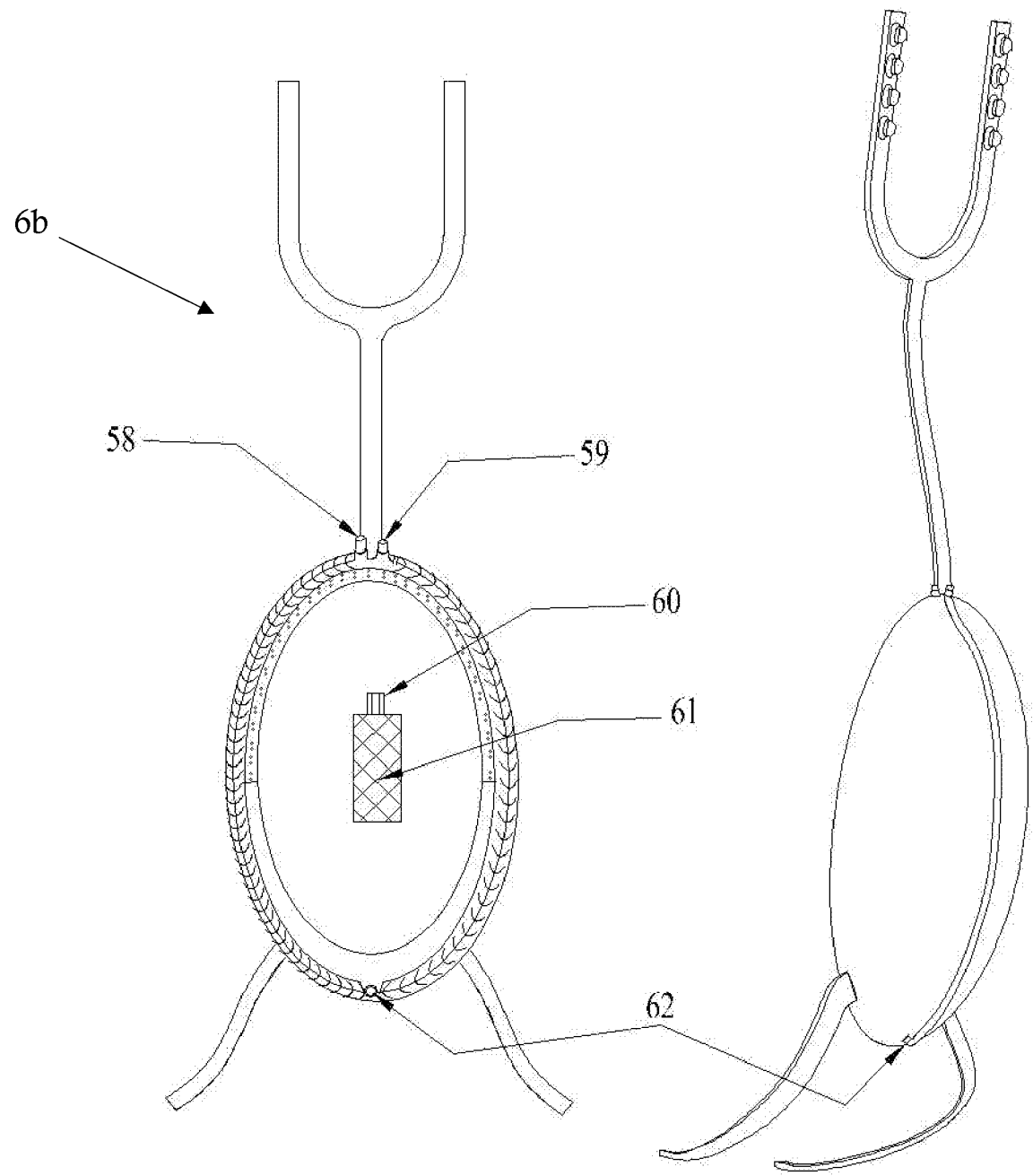

Now referring to FIG. 2b, a back view of an auto sucking female urinary external catheter 6b is provided. The female urinary external catheter 6b has an inlet 59 for water allowing the water to flow from the urine collection device 17 to the urinary area of the female subject through an auto pump 3 and urine pump outlet 58 for pumping the urine from the female urinary external catheter 6b to the urine collection device 17 through the auto pump 3. The urine enters the urinal basin of the female urinary external catheter 6b and as the urine enters; it is sensed by the sensor patch 61 and sends the signal to the auto pump 3 which sucks the urine from the urine sucking hole 62 to the urine collection device 17. The sensor patch 61 is a disposable sensing patch having a connector patch 60 attached to an auto pump 3.

Figure 3A:
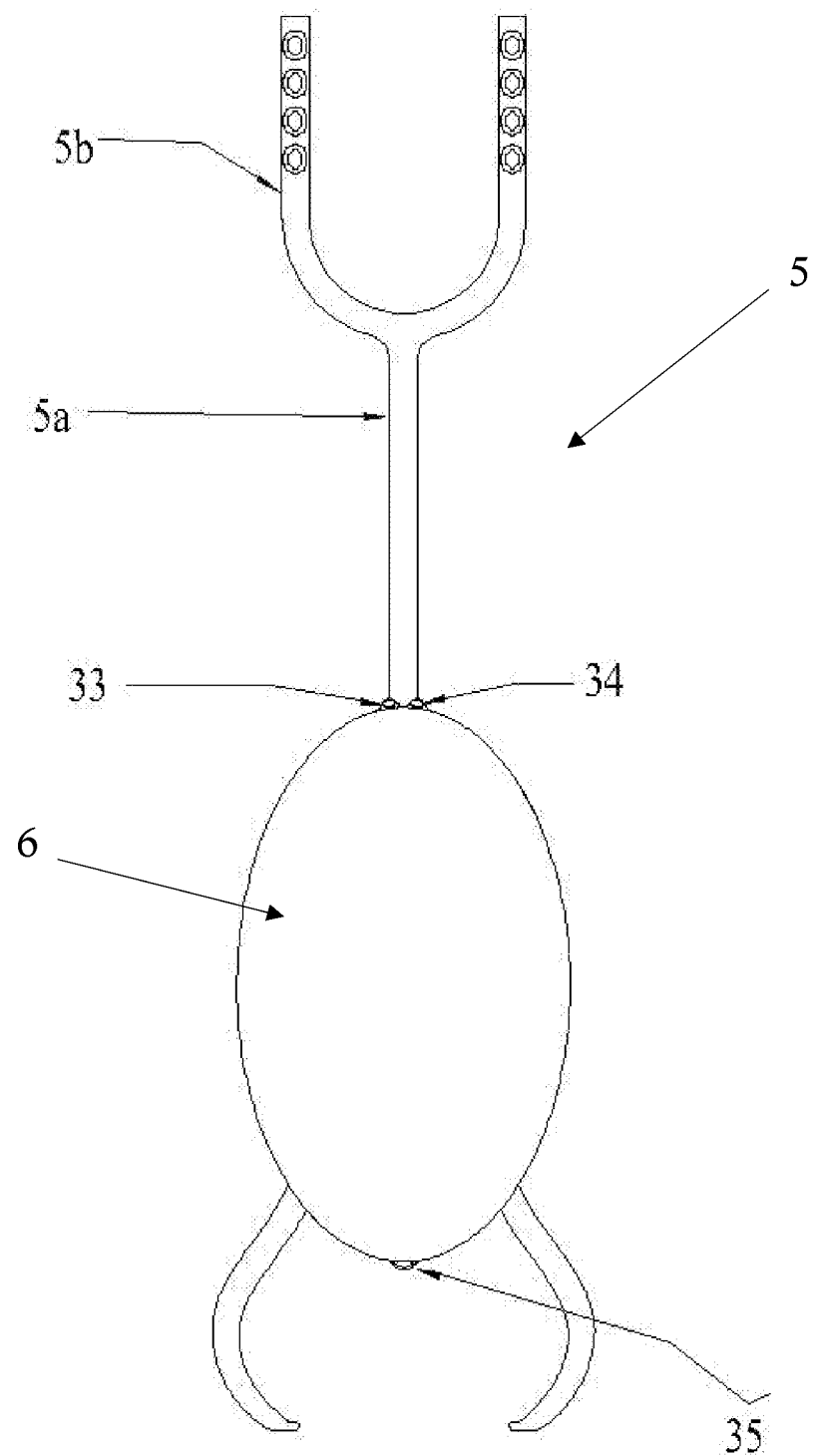
FIGS. 3a, 3b and 3c is a front, back and side view of a stabilizer respectively in accordance to the embodiment of the present invention.
Figure 3B:
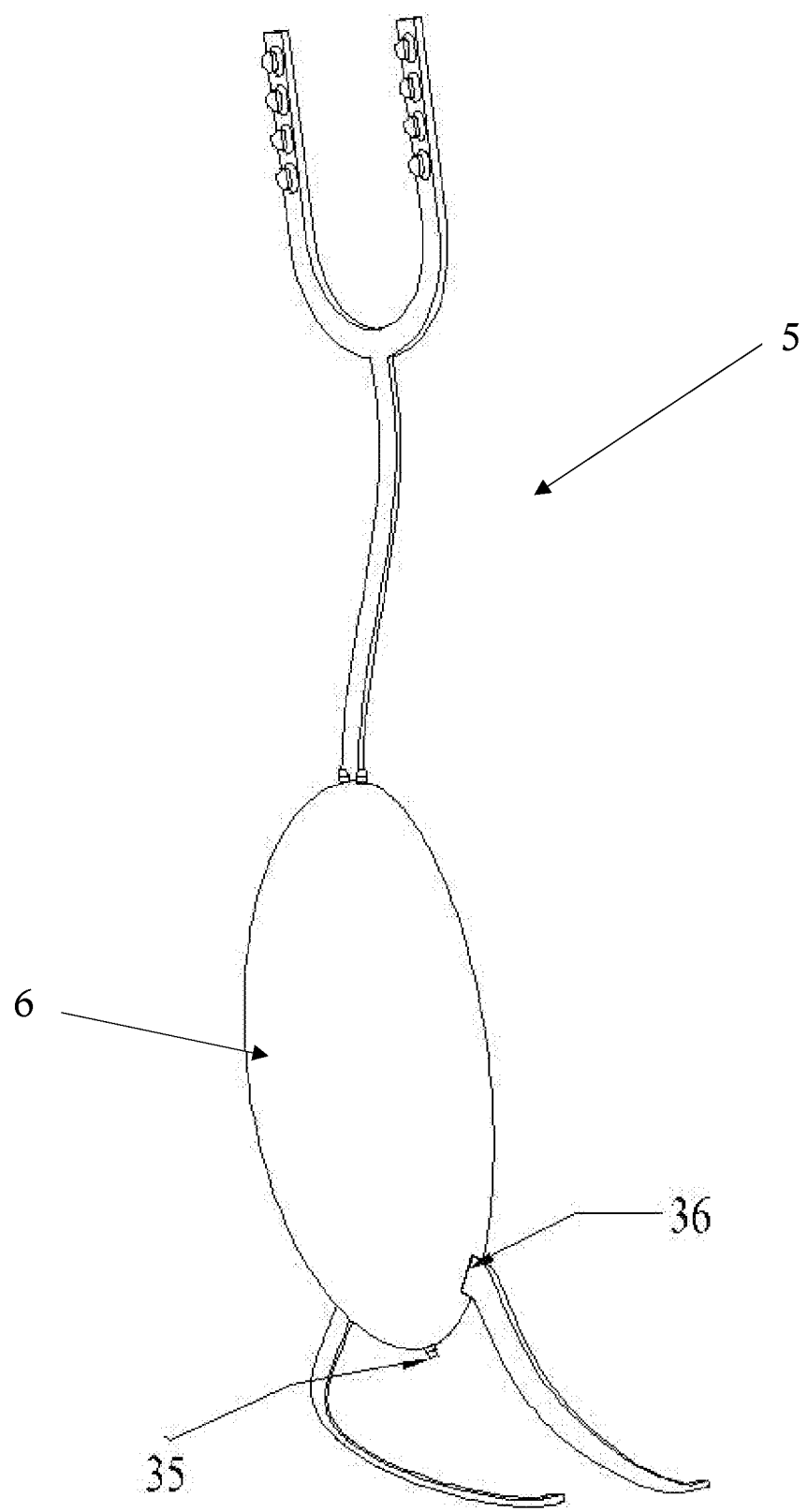
Figure 3C:
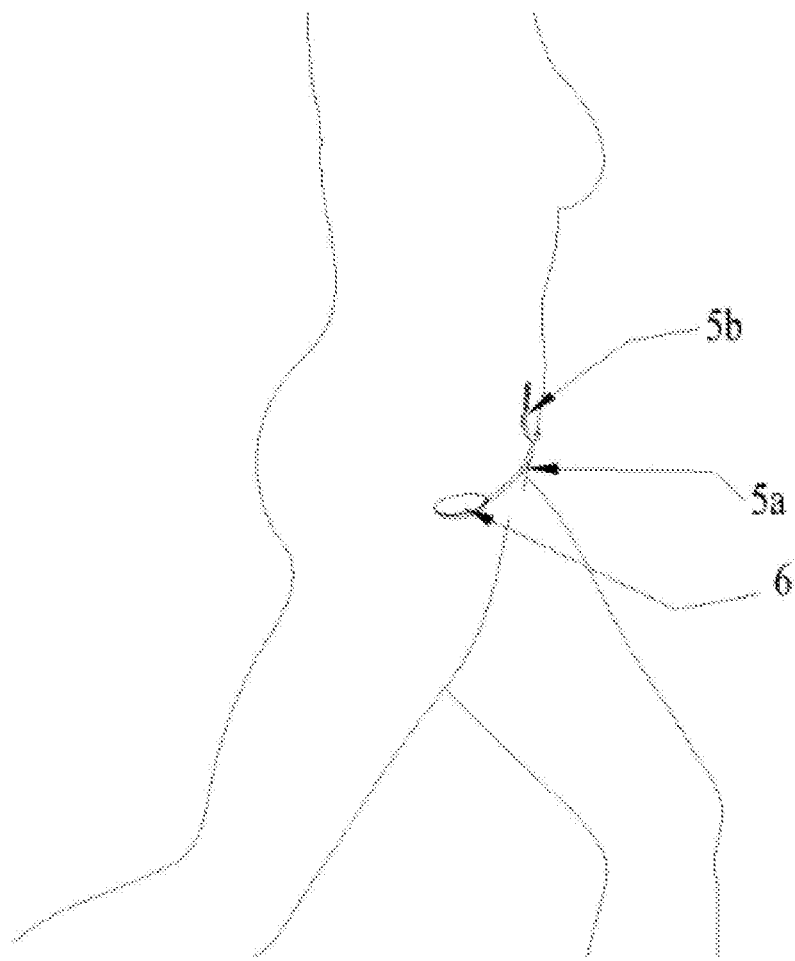

Now referring to FIGS. 3a, 3b and 3c, the front view, side view and back view of stabilizer 5 is provided. The stabilizer 5 having a stabilizer forked end 5b, an oval end 6 and a stabilizer arm 5a to connect said forked end 5b and said oval end. The stabilizer oval end 6 act as a cover for covering the jelly wall of the female urinary external catheter 6a, 6b. The oval end 6 has a concave surface and a convex surface. The convex surface in one embodiment has a water hole 34 in for fitting the water inlet 59 of the external catheter 6b and a urine hole 33 for fitting the urine outlet 58 of the auto sucking female urinary external catheter 6b. The convex surface also has a urine outlet hole 35 to fit the urine sucking hole 62 of the external catheter 6b. The convex surface in another embodiment has a water hole 34 for fitting the water inlet 14 of the external female external catheter 6a and has a urine hole 35 to fit the urine outlet 15 and air vent 102 of the female urinary external catheter 6a. The stabilizer 5 being flexible has a right angle that helps the female external catheter to be well stuck to the genitals by the bending resistance.

Hence, the present provides a female external catheter system 1 comprising: a urinary external catheter 6b to allow urine to pass down without any obstruction; a stabilizer 5 to support and hold the urinary external catheter 6b as per contour of female genitalia; a urine collection device 17 device to collect urine and store fluid for cleaning urinary area of a female subject; and an information collection system to collect and displays characteristics of urine flow; characterized in that, said urine external catheter 6b comprises a holding apparatus, an isolation chamber 25, an inlet 59, a patch sensor 61, an outlet 58 and a plurality of strap 29; a stabilizer comprises a forked end 5a, an oval end 6 and an arm 5b connecting said forked end 5a and said oval end 6, said oval end 6 having a convex surface facing away from the body and a concave surface facing towards body of female, and a belly sticker 101; said urine collection device 17 comprises an auto-driven pump 3, a data transmitter chip and a urine flowmeter located in the tube for sucking the urine/water connected to said information collection system which is preferably a mobile with an in built application. The holding apparatus has an inflatable wall 23 and a jelly wall 19 bordered around a urethral orifice 24, an isolation chamber 25 that allows the urine to pass towards the urine collection device 17, a spraying apparatus 21 to direct the water to wash the urinary area of female subject, an outlet acting as urine sucking hole 62 and a sensor patch 61 to sense the urine in the isolation chamber 25. The urine is sucked from an auto-driven pump 3 through the urine sucking hole 62.

Figure 4:
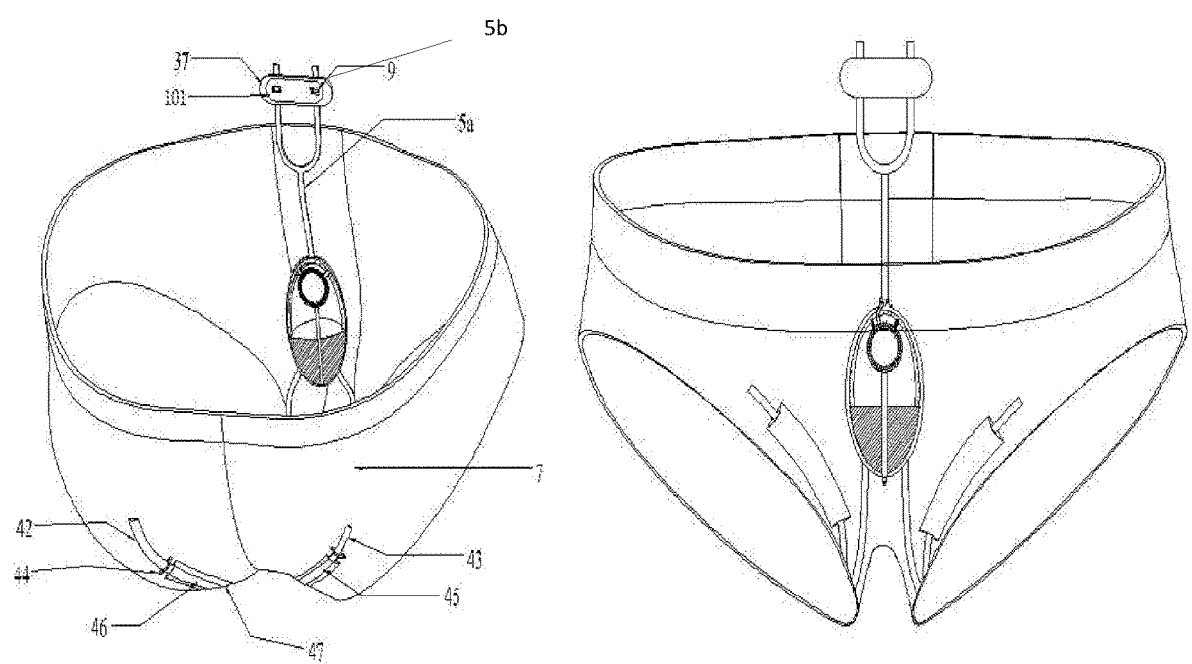
FIG. 4 is a hidden view of customized underwear in accordance to the embodiment of the present invention.

Now referring to FIG. 4, the hidden view of the customized underwear is provided. The customized underwear is special underwear 7 integrated with a urine management system. The urine management system has a stabilizer. The stabilizer 5 has a stabilizer forked end 5b, a stabilizer arm 5a to support the female urinary external catheter 6a, 6b and a stabilizer oval end 6 acting as a covering to female urinary external catheter 6a, 6b. The stabilizer forked end 5b has different fork level connections for adjusting the height of stabilizer with respect to the body. The fork level connections have different level locks 9 which get snap locked to the slots of a belly sticker 101 and said belly sticker is fixed on the body by a breathable adhesive 37. The customized underwear 7 has underwear strap channel 47 which gets strapped to the Velcro straps 29 of the female urinary external catheter 6a, 6b having a back right Velcro strap 43 and a back right silicon strap 45 and the Velcro straps 29 having a back left Velcro strap 42 and a back left silicon strap 46. The connection 44 for connecting the Velcro strap to the silicone strap.

Figure 5:
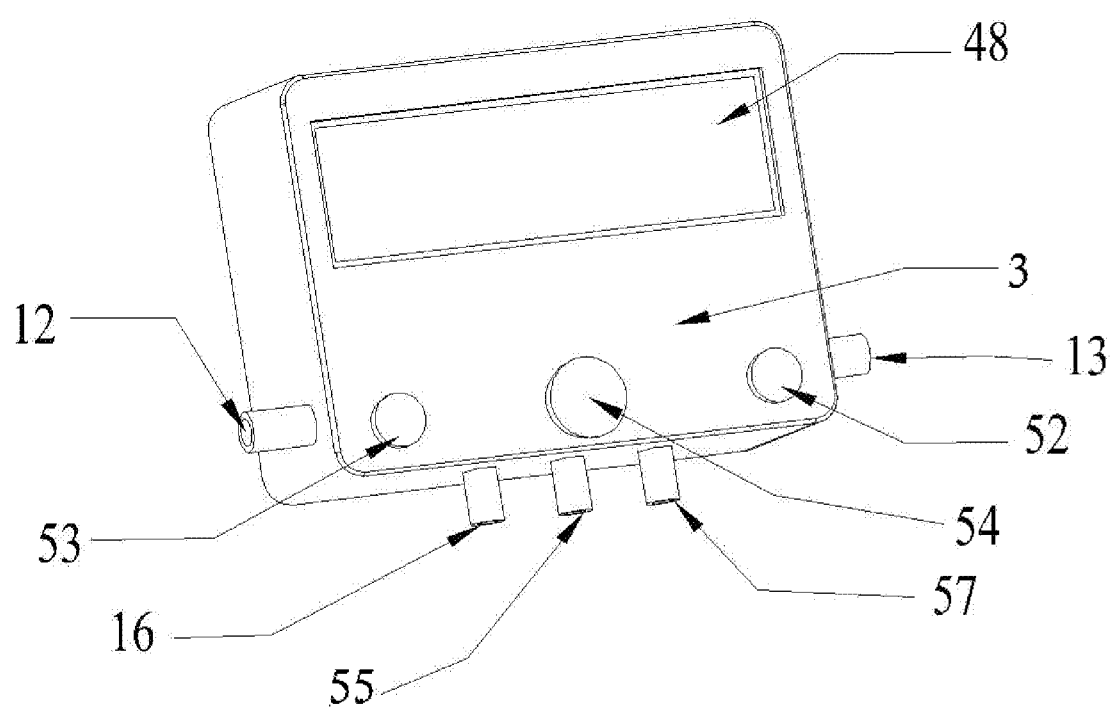
FIG. 5 shows an auto two-way pump for urine/water belt in accordance to the embodiment of the present invention.

Now referring to FIG. 5, the auto two-way pump is provided. The auto pump 3 draws energy from the removable rechargeable battery 48 and is operated automatically by on/off buttons. The auto pump 3 has a urine sucking tube 16 for sucking the urine from the female urinary external catheter 6a, 6b to the urine collection device 17 and being operated by on/off urine sucking button 53. The auto pump 3 has a water pushing tube 55 for pushing the water from the urine collection device 17 to the female urinary external catheter 6a, 6b being operated by on/off water push button 52. The auto pump 3 has an air pumping tube 57 for pumping the air to the inflated wall of the female urinary external catheter 6a, 6b being operated by on/off air pumping button 54. The auto pump 3 has a urine outlet to drain the urine to the urine collection device 17 and water supplier tube 13 for supplying the water to the female urinary external catheter 6a, 6b.

Figure 6:
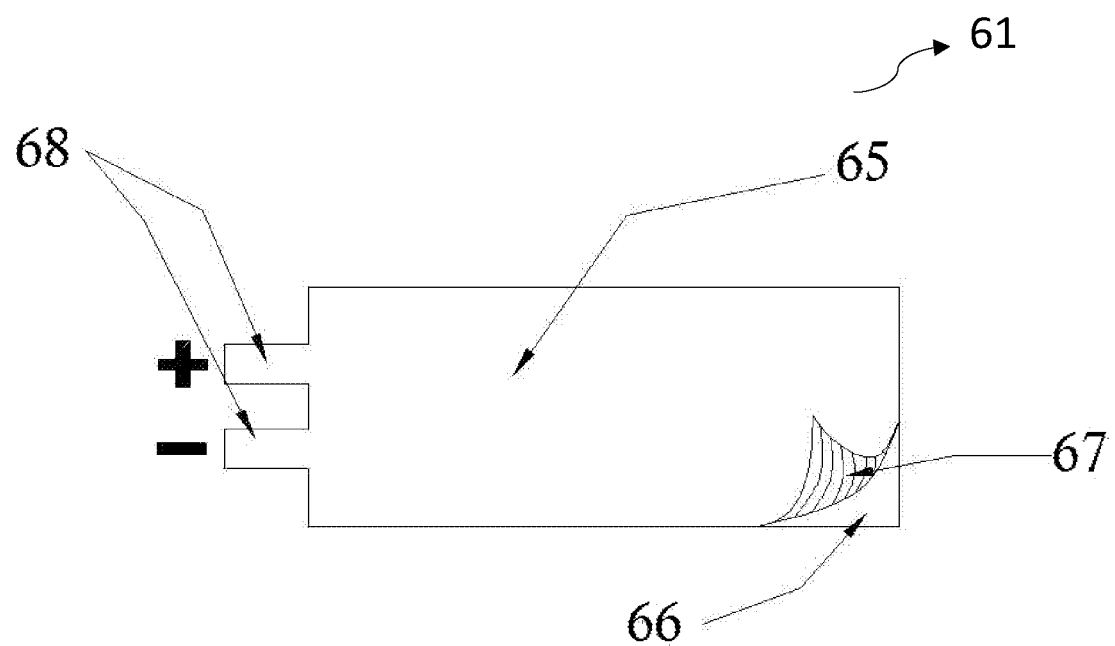
FIG. 6 shows a fluid sensor patch in accordance to the embodiment of the present invention.

Now referring to FIG. 6, the fluid sensor patch is provided. The fluid sensor patch 61 has a conducting patch 65 gets fixed to the adhesive patch 66 by the way of adhesive 67. The patch has an electric strap 68 which gets connected to the auto pump 3.

Figure 7:
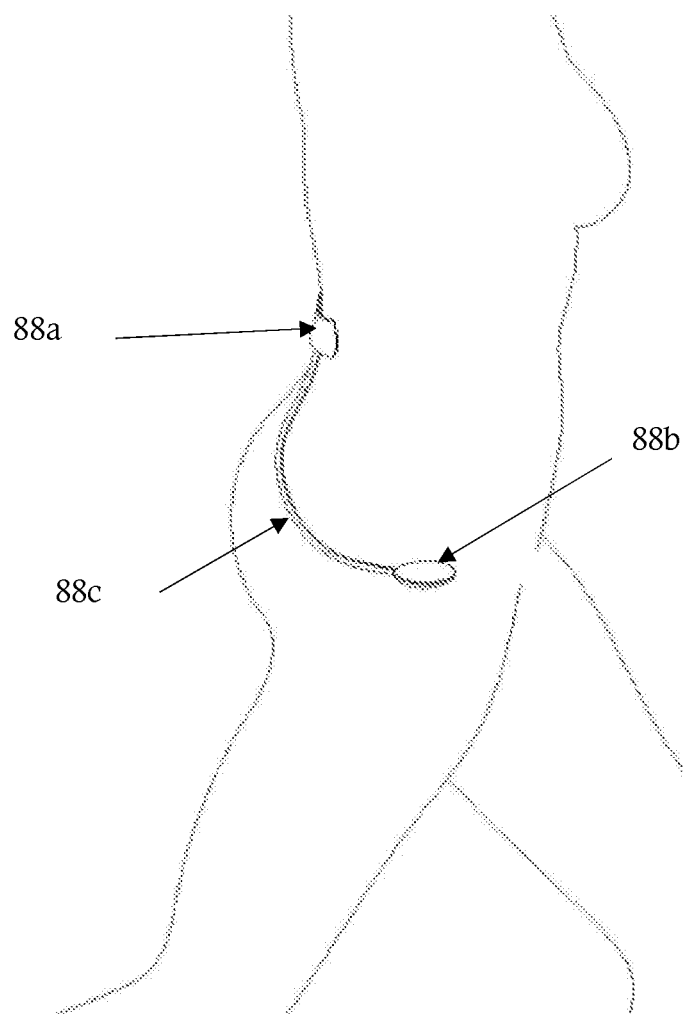
FIG. 7 shows a back stabilizer in accordance with an alternative embodiment of stabilizer in the present invention.

Now referring to FIG. 7, the back stabilizer is provided with a flat end 88a, an oval end 88b and a stabilizer arm 88c to connect said flat end 88a and said oval end 88b. The stabilizer oval end act 88b as a cover for covering the jelly wall of the female urinary external catheter. The oval end 88b has a concave surface holding a female urinary external catheter facing towards the body of the subject and a convex surface facing away from the body of the subject. The stabilizer to be placed on the back side of the female subject has an arm 88c with an acute angle ranging from 70-90 degree of bending that helps the female external catheter to be well stuck to the genitals by the bending resistance. Said flat end 88c of the stabilizer has a sticker which gets fixed on the back side of the female subject by a breathable adhesive.

Figure 8A:
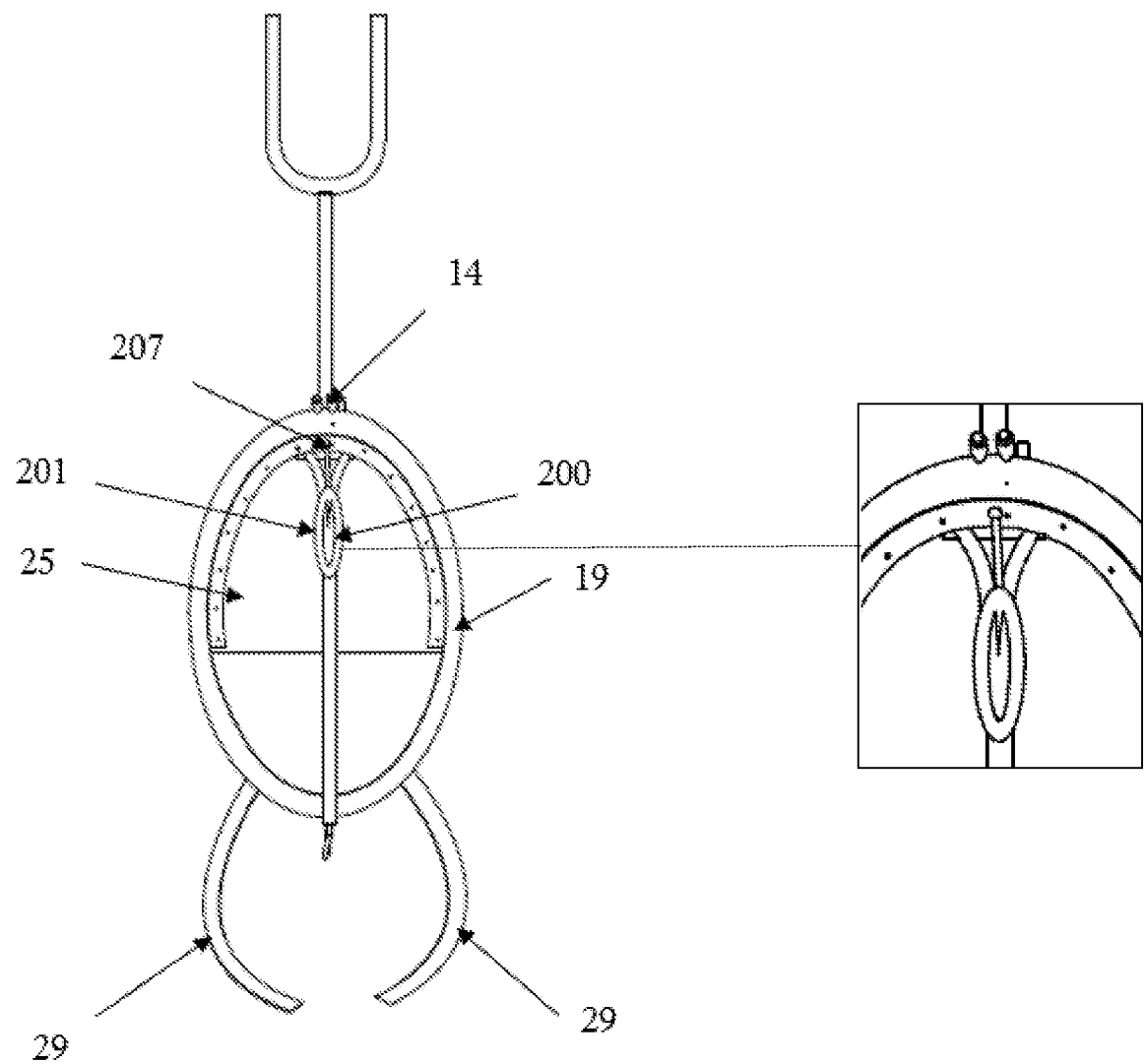
FIGS. 8a and 8b shows a back view and side view of the external catheter for female subject with moderate or low urinary incontinence is provided in accordance with an embodiment of the present invention.
Figure 8B:
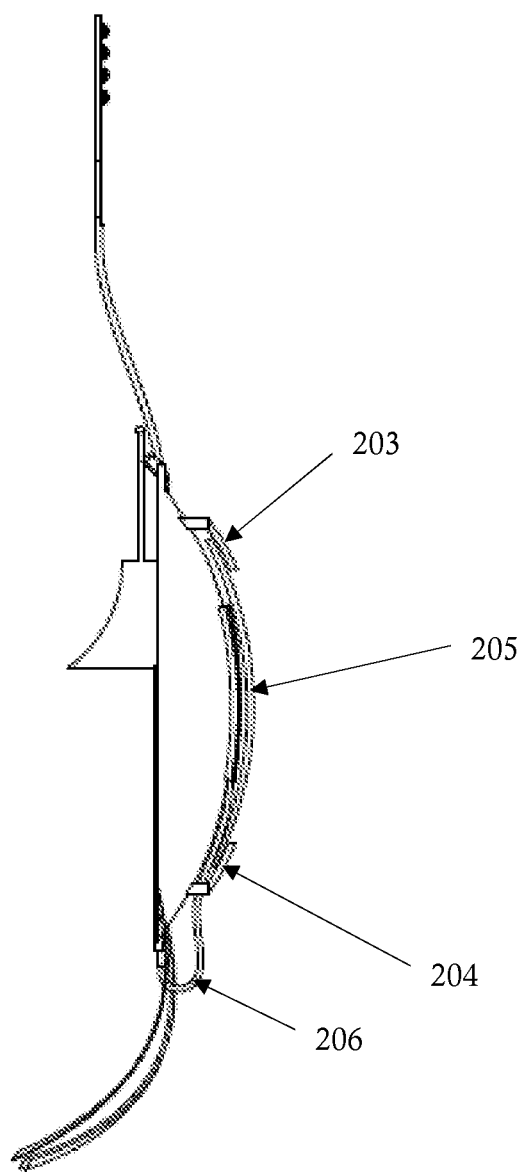

Now referring to FIG. 8a, 8b, a back view and side view of the external catheter for female subject with moderate or low urinary incontinence is provided in accordance with an embodiment of the present invention. The female urinary external catheter 6c comprises a holding apparatus comprising a collapsible wall 200 and a soft jelly wall 201 preferably made of silicone surrounding the collapsible wall 200 forming an outer surface of the external female urinary external catheter 6c. The collapsible wall 200 with the jelly outer wall 201 surrounding is a shape resistant wall preferably made of mildly hard PVC which is curved at the bottom and folded in a zig zag pattern at the top connected to a push/pull pin 207 which when pulled opens up the collapsible opening and fits in the outer labia around the urethral orifice. When the push/pull pin 207 is pushed the collapsible opening closes up. The female urinary external catheter 6c has an inlet 14 for water for directing the water from the pump to the external catheter for spraying water to the urinary area of the female body. The collapsible wall 200 when open forms the urethral orifice that fits into the outer labia of the female genitalia. The low flow of urine or drops of urine when flows from the urethral orifice 24 enters the isolation chamber 25 which is an urinal basin gets drained or absorbed from the isolation chamber 25 through an extension line/string connected to the urine collection device. The extension line/string is a string of highly absorbent polymer inserted in the outlet 28. The collapsible wall 200 is made of jelly outer wall 201 surrounding a shape resistant wall 202 preferably made of mildly hard PVC. With help of this collapsible wall 200, the female subject is able to wear the female urinary external catheter 6c in a closed position and then open the collapsible wall 200 for a comfortable fit. The jelly wall 19 and jelly outer wall 201 is preferably made of silicone. The jelly wall 19 is made of silicone and aids the cushioning effect to the urinary area of the female subject. The lower portion of the female urinary external catheter 6c is a covered area 26. The strap 29 is attached to the outer lower portion of the female urinary external catheter 6c. The strap 29 used is preferably a Velcro strap.

Figure 8C:
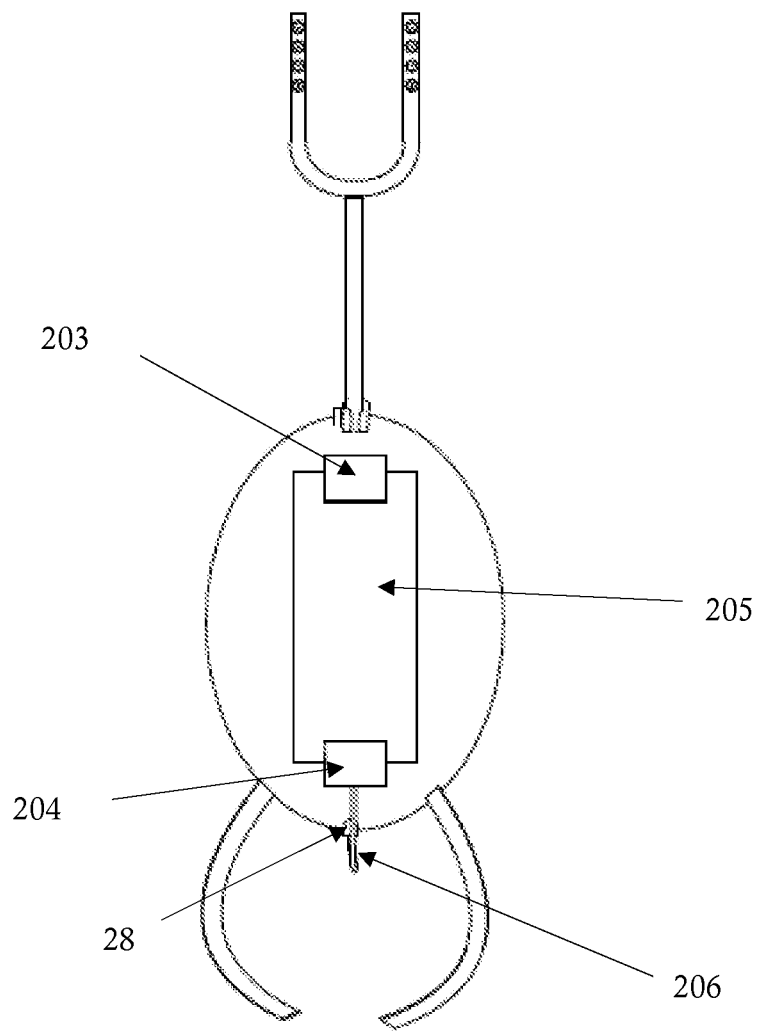
FIG. 8c shows a front view of the external catheter for female subject with moderate or low urinary incontinence is provided in accordance with an embodiment of the present.

FIG. 8c is the front view of the external catheter for female subject with moderate or low urinary incontinence is provided in accordance with an embodiment of the present invention. The female external urinary catheter 6c at the front portion has an upper pad holder 203 and a lower pad holder 204 to hold the highly absorbent disposable pad 205 with an extension line/string 206 that is inserted into the outlet 28 to absorb urine in the isolation chamber.

Hence, the present invention provides a female external catheter system 1 for female subject with moderate to low urinary incontinence comprising: a urinary external catheter 6c to allow urine to pass down without any obstruction; a stabilizer 5 to support and hold the urinary external catheter 6c as per contour of female genitalia; a urine collection device 17 device to collect urine; characterized in that, said urine external catheter 6c comprises a holding apparatus, an isolation chamber 25, an inlet 14, an outlet 28 and a plurality of strap 29; a stabilizer 5 comprises a forked end 5a, an oval end 6 and an arm 5b connecting said forked end 5a and said oval end 6, said oval end 6 having a convex surface facing away from the body and a concave surface facing towards the body, and a belly sticker 101; said urine collection device 17 is a highly absorbent disposable pad 205 enclosed in a water resistant cover with an extension line 206 that comes in contact with the urine inside the isolation chamber 25 and absorbs and eventually moved to the pad 205. The holding apparatus has a collapsible wall 200 and a jelly outer wall 201 bordered around a urethral orifice 24, an isolation chamber 25 that allows the urine to pass towards the urine collection device 17. The female external urinary catheter 6c at the outer portion has an upper pad holder 203 and a lower pad holder 204 to hold the highly absorbent disposable pad 205 with an extension line 206 that is inserted into the outlet 28 to absorb urine in the isolation chamber 25. The collapsible wall 200 surrounded by jelly outer wall 201 is a shape resistant wall preferably made of mildly hard PVC which is curved at the bottom and folded in a zig zag pattern at the top connected to a push/pull stick which when pulled opens up the collapsible wall 200 and fits in the outer labia around the urethral orifice 24 and when the push/pull stick is pushed the collapsible wall closes up.

The following reference numerals are used for referring to various components of the device as shown in drawings.

| | |
|---|---|
| 1: female external catheter system | 10: Belt lock |
| 6a, 6b, 6c: Female urinary external catheter | 18: Inlet |
| | 8: Outlet |
| 17: Waist Belt | 4: Water pushing tube |
| 7: Customized Underwear | 16: Urine sucking tube |
| 14: Inlet for water/Water inlet | 12: Urine outlet |
| 3: Auto pump | 13: Water supplier tube |
| 15: Outlet for Urine/Urine outlet | 23: Inflatable wall |
| 17: Urine collection device | 24: Urethral Orifice |
| 5: Stabilizer | 25: Isolation chamber |
| 6: Oval end | 28: Urine outlet |
| 9: Locks | 19: Soft jelly wall |
| 101: Belly sticker | 21: Spraying apparatus |
| 2: Vertical chambers | 102: Air vent |
| 11: Vertical chambers | 50: Urinal connect |

-continued

| | |
|---|---|
| 26: Covered area | 43: back right Velcro strap |
| 27: Air discharge tube | 45: back right silicon strap |
| 29: Strap | 42: back left Velcro strap |
| 30: Strap connection | 46: back left silicon strap |
| 6b: Female urinary external catheter | 44: connection |
| 58: Urine outlet | 48: removable rechargeable battery |
| 59: Inlet | 53: urine sucking button |
| 60: Connector patch | 52: water push button |
| 61: Sensor patch | 57: air pumping tube |
| 62: Urine sucking hole | 54: air pumping button |
| 65: Conducting patch | 88a: flat end |
| 66: Adhesive patch | 88b: oval end |
| 67: Adhesive | 88c: stabilizer arm |
| 68: Electric strap | 200: Collapsible wall |
| 5a: Stabilizer arm | 201: Jelly outer wall |
| 5b: Stabilizer forked end | 203: Upper pad holder |
| 33: Urine hole | 204: Lower pad holder |
| 34: Water hole | 205: Disposable pad |
| 35: Urine outlet hole | 206: Extension line |
| 37: Breathable adhesive | 207: Push/pull stick |
| 47: underwear strap channel | |

We claim:

1. A female external catheter system (1) comprising:
a urinary external catheter (6a) to allow urine to pass down without any obstruction;
a stabilizer (5) to support and hold the urinary external catheter (6a) as per contour of female genitalia; and
a urine collection device (17) to collect urine and store fluid for cleaning urinary area of a female subject;
characterized in that,
said urinary external catheter (6a) is wearable and comprises of a holding apparatus, an isolation chamber (25), a spraying apparatus (21), a plurality of inlets (14), an air vent (102), an outlet (15), an air discharge tube (27) and a plurality of strap (29);
said stabilizer (5) comprises of a forked end (5b), an oval end (6) and an arm (5a) connecting the forked and the oval end, said oval end (6) having a convex surface facing away from the body and a concave surface facing towards body of female, and a belly sticker (101);
said urine collection device (17) is a multi-chambered device attached to an auto-driven pump (3) attached to it to push the water from the urine collection device (17) for washing and to suck the urine out from the urinary external catheter (6a).

2. The system as claimed in claim 1, wherein, the holding apparatus has an inflatable wall (23) and jelly wall (19) bordered around a urethral orifice (24), an isolation chamber (25) allows the urine to pass towards the urine collection device (17), an air vent (102) to push the air from the external catheter (6a), a spraying apparatus (21) to direct the water to wash the urinary area of female subject.

3. The system as claimed in claim 1, wherein, the convex surface has plurality of holes (34, 35) to fit into the plurality of holes of urinary external catheter (6a).

4. The system as claimed in claim 1, wherein, the urine collection device (17) is an external urine bag or in the form of belt worn around the waist of female subject.

5. The system as claimed in claim 1, wherein optionally a back stabilizer is used with a flat end 88a, an oval end 88b and a stabilizer arm 88c to connect said flat end 88a and said oval end 88b.

6. A female external catheter system 1 comprising:
a urinary external catheter (6b) to allow urine to pass down without any obstruction;
a stabilizer (5) to support and hold the urinary external catheter (6b) as per contour of female genitalia;
a urine collection device (17) device to collect urine and store fluid for cleaning urinary area of a female subject; and
an information collection system to collect and displays characteristics of urine flow;
characterized in that,
said urine external catheter (6b) comprises a holding apparatus, an isolation chamber (25), an inlet (59), a patch sensor (61), an outlet (58) and a plurality of strap (29);
a stabilizer comprises a forked end (5a), an oval end (6) and an arm (5b) connecting said forked end (5a) and said oval end (6), said oval end (6) having a convex surface facing away from the body and a concave surface facing towards body of female, and a belly sticker (101);
said urine collection device (17) comprises an auto-driven pump (3), a data transmitter chip and a urine flowmeter located in the tube for sucking the urine/water connected to said information collection system which is preferably a mobile with an in built application.

7. The system as claimed in claim 6, wherein, the holding apparatus has an inflatable wall (23) and a jelly wall (19) bordered around a urethral orifice (24), an isolation chamber (25) that allows the urine to pass towards the urine collection device (17), a spraying apparatus (21) to direct the water to wash the urinary area of female subject, an outlet acting as urine sucking hole (62) and a sensor patch (61) to sense the urine in the isolation chamber (25).

8. The system as claimed in claim 7, wherein, the urine is sucked from an auto-driven pump (3) through the urine sucking hole (62).

9. The system as claimed in claim 6, wherein optionally a back stabilizer is used with a flat end 88a, an oval end 88b and a stabilizer arm 88c to connect said flat end 88a and said oval end 88b.

10. A female external catheter system 1 for female subject with moderate to low urinary incontinence comprising:
a urinary external catheter (6c) to allow urine to pass down without any obstruction;
a stabilizer (5) to support and hold the urinary external catheter (6c) as per contour of female genitalia;
a urine collection device (17) device to collect urine;
characterized in that,
said urine external catheter (6c) comprises a holding apparatus, an isolation chamber (25), an inlet (14), an outlet (28) and a plurality of strap (29);
a stabilizer (5) comprises a forked end (5a), an oval end (6) and an arm (5b) connecting said forked end (5a) and said oval end (6), said oval end (6) having a convex surface facing away from the body and a concave surface facing towards the body, and a belly sticker (101);
said urine collection device (17) is a highly absorbent disposable pad (205) enclosed in a water resistant cover with an extension line (206) that comes in contact with the urine inside the isolation chamber (25) and absorbs and eventually moved to the pad (205).

11. The system as claimed in claim 10, wherein, the holding apparatus has a collapsible wall (200) and a jelly outer wall (201) bordered around a urethral orifice (24), an isolation chamber (25) that allows the urine to pass towards the urine collection device (17).

12. The system as claimed in claim 10, wherein, the female external urinary catheter (6c) at the outer portion has an upper pad holder (203) and a lower pad holder (204) to hold the highly absorbent disposable pad (205) with an extension line (206) that is inserted into the outlet (28) to absorb urine in the isolation chamber (25).

13. The system as claimed in claim 10, wherein, the collapsible wall (200) surrounded by jelly outer wall (201) is a shape resistant wall preferably made of mildly hard PVC which is curved at the bottom and folded in a zig zag pattern at the top connected to a push/pull stick which when pulled opens up the collapsible wall (200) and fits in the outer labia around the urethral orifice (24) and when the push/pull stick is pushed the collapsible wall closes up.

14. The system as claimed in claim 10, wherein optionally a back stabilizer is used with a flat end 88*a*, an oval end 88*b* and a stabilizer arm 88*c* to connect said flat end 88*a* and said oval end 88*b*.

* * * * *